US006449509B1

United States Patent
Park et al.

(10) Patent No.: US 6,449,509 B1
(45) Date of Patent: Sep. 10, 2002

(54) IMPLANTABLE STIMULATION DEVICE HAVING SYNCHRONOUS SAMPLING FOR A RESPIRATION SENSOR

(75) Inventors: Euljoon Park, Stevenson Ranch, CA (US); Gene A. Bornzin, Simi Valley, CA (US); Joseph J. Florio, La Canada, CA (US); Said Mortazavi, Sherman Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 124 days.

(21) Appl. No.: 09/651,623

(22) Filed: Aug. 30, 2000

(Under 37 CFR 1.47)

(51) Int. Cl.⁷ .............................................. A61N 1/365
(52) U.S. Cl. ......................... 607/20; 607/17; 600/547; 600/533
(58) Field of Search ................................. 607/9, 17, 19, 607/20; 600/509, 513, 519, 521, 533, 534, 536, 547, 483–484; 128/901

(56) References Cited

U.S. PATENT DOCUMENTS 4,870,578 A * 9/1989 Vysin et al. ................ 600/484
5,876,353 A * 3/1999 Riff ............................ 600/529

* cited by examiner

Primary Examiner—Kennedy Schaetzle
Assistant Examiner—Kristen Droesch (57) ABSTRACT

An implantable cardiac device that is adapted to periodically measure a body parameter, such as transthoracic impedance, at time periods selected so that the body parameter is primarily indicative of the respiration of the patient. In this way, a ventilation parameter, such as minute ventilation, can be reconstructed from the signals without requiring filtering of the sampled signals. In one embodiment, the implantable cardiac device measures transthoracic impedance during each quiescent period of the heart and thereby obtains a plurality of transthoracic impedance data points which are then used to reconstruct a ventilation signal. As the transthoracic impedance data points are obtained during the quiescent period, the contribution of the heart to the resulting transthoracic impedance measurement can be ignored and the resulting measurements are indicative of the action of the heart. In another embodiment, the implantable cardiac device obtains transthoracic impedance signals during the zero crossings of the measured impedance signal. As the transthoracic signal is measured during the zero crossing of the measured impedance signal, the heart component of the signal is filtered out.

42 Claims, 6 Drawing Sheets

IMPLANTABLE STIMULATION DEVICE HAVING SYNCHRONOUS SAMPLING FOR A RESPIRATION SENSOR

FIELD OF THE INVENTION

The present invention relates generally to cardiac pacemakers, and other types of implantable medical devices, which provide electrical stimuli to the heart to control the heart's rhythm. More particularly, the invention relates to isolating the respiration signal from the heart signal without the use of filters.

BACKGROUND OF THE INVENTION

Cardiac pacing involves the electrical stimulation of the heart in order to control the timing of the contractions of the heart. Electrical stimuli in the form of pulses are generated by a battery-powered pacemaker and applied to the tissue of the heart by one or more electrodes that are connected to the pacemaker via flexible, insulated conductors. The insulated conductors and associated electrodes form what is referred to as the "lead."

Some pacemakers deliver cardiac stimulating pulses at a fixed, programmed rate regardless of the patient's activity level. Although this technique may be adequate for some, other patients respond better if the pacing system adapts the delivery of the cardiac stimulating pulses based upon the patient's metabolic demand. In these systems, as metabolic demand increases, the rate of cardiac pacing also increases. These "rate adaptive" pacing systems need to be able to detect when metabolic demand is changing.

A respiratory-related parameter, which has been found to closely correlate with metabolic demand, is minute ventilation. Minute ventilation may be defined as the volume of air inspired and expired by the patient during a predetermined time period. It has been found that minute ventilation tracks very well with metabolic need over a range of heart rates, and, therefore, can provide a good index for a rate adaptive pacemaker. Specifically, as the patient breathes faster, the patient's heart rate should pick up, as the faster breathing is often indicative of greater physical activity. However, the techniques used to derive the minute ventilation signal in prior art devices are often contaminated by events other than respiratory activity.

Minute ventilation can be calculated from a measured transthoracic impedance. For example, the transthoracic impedance is often measured between an intracardiac lead implanted in the heart and the case electrode that is implanted in the patient's body, e.g., under the patient's pectoral muscle. Measuring the transthoracic impedance using the pacing leads and the case electrode usually presents an undesired heart component in the minute ventilation signal. In particular, the beating of the heart results in a component of the transthoracic impedance being related to the motion of the heart rather than the motion of lungs as a result of the patient inhaling and exhaling. This component of the minute ventilation parameter may be significant enough to result in the pacemaker processor erroneously concluding that the minute ventilation signal is indicative of a false activity level for the patient.

Hence, to use the minute ventilation signal, the heart component generally must be removed. Currently, the heart component is removed by the use of a sharp filter. Hence, use of a filter adds an additional step to the processing of the minute ventilation signal and consumes additional space in the pacemaker case. Moreover, the filter also results in additional consumption of power from the battery that decreases the long-term life of the implanted device.

The minute ventilation signal can also be obtained by periodically sampling the transthoracic impedance to develop the overall minute ventilation signal. To obtain a properly sampled signal, current pacemakers sample at rates between 16–20 samples per second. The high sampling rate ensures that the minute ventilation waveform is accurately reconstructed over all expected frequencies. Because every sample taken consumes battery power, a high sampling rate of 16–20 samples per second can significantly decrease the battery life of the pacemaker.

Hence, a need exists to obtain the minute ventilation signal using the pacing leads and case, but to avoid the use of a filter to remove the heart signal. Also, it is desirable to decrease the sampling rate to obtain the minute ventilation signal to conserve power from the pacemaker battery, effectively increasing the useable life of the pacemaker. Preferably, the minute ventilation signal should be obtained using only a small amount of power.

SUMMARY OF THE INVENTION

The present invention provides a unique method of isolating the minute ventilation signal from the heart signal using a low sampling rate and without the use of a filter. On average, the heart rate is approximately four times the respiratory rate. For example, a person's heart may beat, on average, sixty times per minute while the same person breathes only sixteen times per minute. The present invention samples the transthoracic impedance, which is indicative of a minute ventilation signal without obtaining a heart signal component by synchronizing the sampling rate with the heart rate.

One technique for sampling the impedance without obtaining a heart component is to provide a sampling rate, which samples the impedance at the zero crossings or during the quiescent periods of the heart signal. Because the heart rate is approximately four times faster than the respiratory rate, sampling at the zero crossing of the heart rate provides adequate data to determine the minute ventilation signal while reducing contributions from the heart signal.

In this embodiment, because the sampling occurs at the zero crossings of the heart signal, there are no significant heart components sampled. Therefore, the majority of the signal sampled is a result of the patient's respiration. By synchronizing the sampling rate with the heart rate, sampling can be selected to only occur when the sampled signal is primarily indicative of respiration and this signal can then be used to produce a minute ventilation parameter. Therefore, the need to filter out the heart signal is eliminated.

In another embodiment, the sampling rate is selected so as to be synchronized with the heart rate such that the transthoracic impedance is sampled at least once each heart cycle at the same interval during the heart signal. If the transthoracic impedance is sampled at the same interval during each heart cycle, the heart's contribution to the impedance signal can be ignored as a constant. The contribution to the transthoracic impedance due to the patient's respiration can then be reconstructed so as to provide the minute ventilation parameter.

The present invention also conserves power by decreasing the sampling rate. Because the sampling rate is synchronized such that the heart signal component can be ignored, a sampling rate of approximately twice the heart rate will obtain adequate data. As an average heart rate is 60 beats per minute, or one beat per second, the average sampling rate under the present invention is between 2–4 samples per second. The significant decrease from the 16–20 samples per second used in filter based systems conserves battery power of the pacemaker.

One embodiment of the present invention is a method of sampling a respiratory signal by a pacing system. The method includes the steps of determining a heart signal having a heart rate and establishing a sampling rate at approximately about twice the heart rate. The sampling rate is then synchronized with the heart signal and the respiratory signal sampled at the synchronized sampling rate. This method results in the respiratory signal data being sampled at about the zero-crossings of the heart signal or being sampled at an interval of the heart signal such that the heart signal contribution can be ignored.

Another embodiment of the present invention is a method of determining minute ventilation data by a pacing system. The method includes the steps of detecting the heart signal and sampling the respiratory signal and the heart signal at a sampling rate. The sampling rate is synchronized with the heart rate so the samples are obtained at about approximately the zero crossings of the heart signal, thereby removing the heart component from the respiratory signal without the use of a filter. Alternatively, the sampling rate is selected so that the heart component is essentially a constant for each measurement and can, thus, be ignored. The minute ventilation data is then determined from the respiratory signal. The minute ventilation data is determined by calculating the amplitude times the frequency of the respiration signal.

BRIEF DESCRIPTION OF THE DRAWINGS

These and other features of the invention will now be described with reference to the drawings of certain preferred embodiments, which are intended to illustrate and not limit the invention, and in which.

DETAILED DESCRIPTION OF THE PREFERRED EMBODIMENTS

Figure 1A:
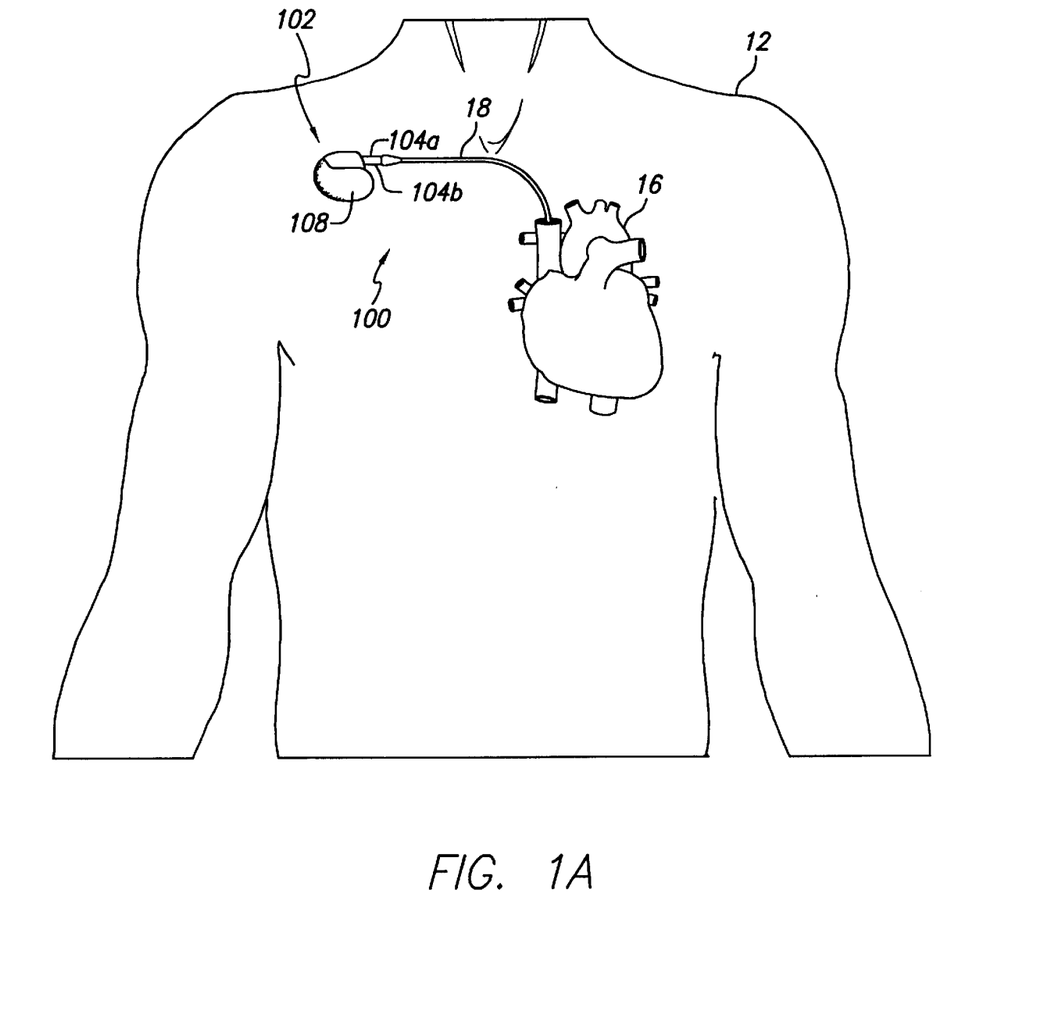
FIG. 1A is an illustration of a pacemaker implanted in a patient.

Referring to FIG. 1A, there is shown an illustration of generally where an implanted cardiac device 100, such as a pacemaker, in accordance with one embodiment of the invention, may be implanted in a patient 12. In accordance with conventional practice in the art, the control unit 102 is housed within a hermetically sealed, biologically inert outer canister or casing 108, which may itself be conductive and thus serve as an indifferent electrode in the pacemaker's pacing/sensing circuit as will be described in greater detail below.

One or more pacemaker leads, collectively identified with reference numerals 104a (ventricular) and 104b (atrial) in FIG. 1A are electrically coupled to the control unit 102 in a conventional manner, extending into the patient's heart 16 via a vein 18. Disposed generally near the distal end of leads 104a and 104b are one or more exposed conductive electrodes for receiving electrical cardiac signals and/or for delivering electrical pacing stimuli to the heart 16. As will be appreciated by those of ordinary skill in the art, leads 104a and 104b may be implanted with their distal end situated in either the atrium or ventricle of the heart 16.

Figure 1B:
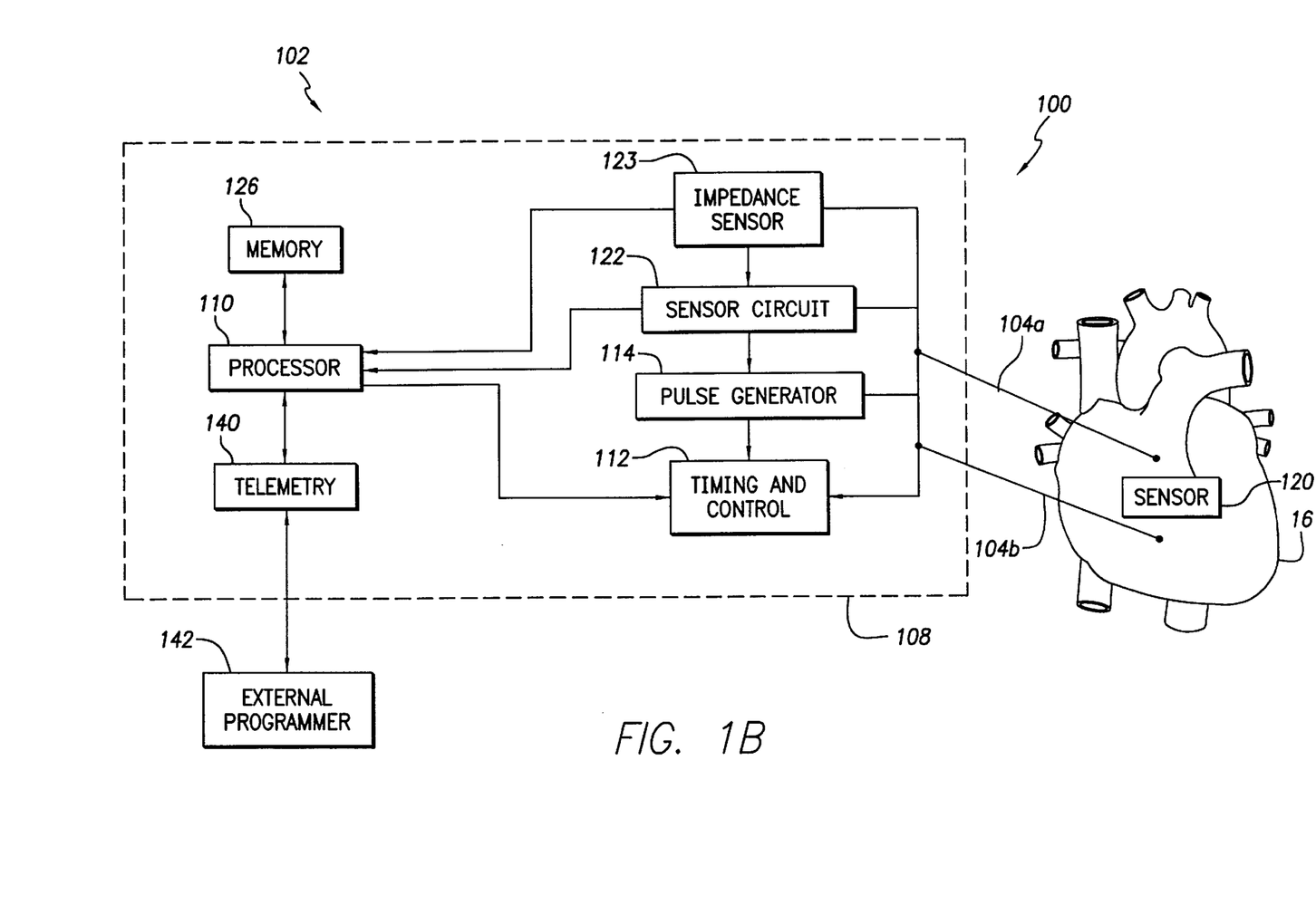
FIG. 1B is a block diagram of one embodiment of an implantable cardiac device according to the present invention.

FIG. 1B is a functional block diagram, illustrating one embodiment of an implantable cardiac device 100. The implantable cardiac device 100 incorporates a control unit, generally designated 102, which is generally positioned within the casing 108 (FIG. 1A), and a plurality of leads 104a and 104b that are configured to be positioned within the chamber of a patient's heart 16. In the embodiment shown in FIG. 1B, the implantable cardiac device 100 includes the first lead 104a that is configured to be implanted within an atrium of the heart 16 and the second lead 104b that is configured to be implanted within a ventricle of the heart 16.

The control unit 102 includes a processor 110, which provides output signals to a timing and control circuit 112. Upon receipt of the output signals from the processor 110, the timing and control circuit 112 induces, or otherwise controls, a pulse generator 114 to produce therapeutic electrical stimulation that is transported via the leads 104 to thereby stimulate the heart 16. The exact function of the processor 110 in inducing the delivery of the therapeutic electrical stimulation to the heart is performed in any of a number of well-known manners. In one embodiment, the processor 110 triggers pacing pulses to be delivered to the apex of the ventricle of the heart 16. The implantable cardiac device 100 can be comprised of any implantable device, including a pacemaker or an intra-cardioverter defibrillator (ICD), or some implantable device incorporating the functionality of both a pacemaker and an ICD.

Further, the processor 110 receives input signals from a sensor 120 via a sensor circuit 122. In one embodiment, the sensor 120 is actually comprised of an implanted lead 104b that is positioned within one of the chambers of the heart 16 so as to provide an intracardiac electrogram (IEG) signal to the processor 110 in a well-known manner. Hence, the processor 110 is configured to receive a heart signal which is indicative of the activity of the heart 16 and is further configured to provide therapeutic electrical stimulation to the heart based, at least in part, upon the IEG signal.

The processor 110 of the embodiment shown in FIG. 1B is also capable of communicating via a telemetry circuit 140 with an external programmer 142. As is understood in the art, the telemetry circuit 140 typically includes an RF signal generator and an RF signal receiver that communicates with a matching RF signal generator and RF signal receiver on the programmer 142. Instructions can be downloaded into the processor 110 to configure the processor 110 to provide particular types of therapy to the heart 16. Further, information and data stored in the memory 126 can be uploaded by the processor 110 via the telemetry circuit 140 to the external programmer 142. This allows treating physicians to retrieve information stored in the memory 126 indicative of the functioning of the implantable electrical device or the heart 16 during particular episodes.

In all of the foregoing aspects, the function and operation of the implantable cardiac device 100 is substantially the same as the function and operation of similar implantable cardiac devices of the prior art. Moreover, a person of ordinary skill in the art will appreciate that the configuration of the implantable cardiac device shown in FIG. 1B is simply illustrative of one possible configuration and the exact configuration and operation of the device can vary from patient to patient without departing from the spirit of the present invention.

To determine activity levels of the patient, minute ventilation-sensing, rate-adaptive pacing systems have been demonstrated to provide rate modulation that is closely correlated with oxygen consumption in most patients implanted with these devices. Minute ventilation is estimated by frequent measurements of transthoracic impedance between an intracardiac lead and the pacemaker case.

In this embodiment, the implanted cardiac device 100 also includes an impedance sensor 123, which provides an input signal to the processor 110, which is indicative of the respiration of the patient. In one embodiment, the impedance sensor circuit 123 periodically measures the transthoracic impedance between the casing 108 and one of the implanted leads 104a, 104b of the implanted cardiac device 100. As discussed above, transthoracic impedance is a parameter that is known to be indicative of the respiration signal and can be used to provide a minute ventilation parameter.

To obtain this transthoracic impedance, a low-energy pulse of known current amplitude (for example, 1 mA with pulse duration 15 microseconds) can be delivered from a ring electrode of the pacing leads 104. The resultant voltage between the electrode and the pacemaker case 108 can then be measured by the sensor circuit 123 and the impedance calculated by the processor 110. Transthoracic impedance increases with inspiration and decreases with expiration. By measuring the frequency of respiration-related fluctuations in impedance (correlated with respiratory rate) and the amplitude of those excursions (correlated with tidal volume), the estimated minute ventilation can be calculated by the processor 110 in a well-known manner.

When the patient is particularly active, the processor 110 increases the pacing rate of the pacemaker to thereby induce the heart 16 to beat faster thereby providing more blood to the patient's muscles.

Alternatively, when the patient is at rest, the processor 110 reduces the pacing rate so as to conserve power and also so as to have the heart 16 perform in a manner which more closely mirrors the function of normal hearts when the patient is at rest.

Figure 2:
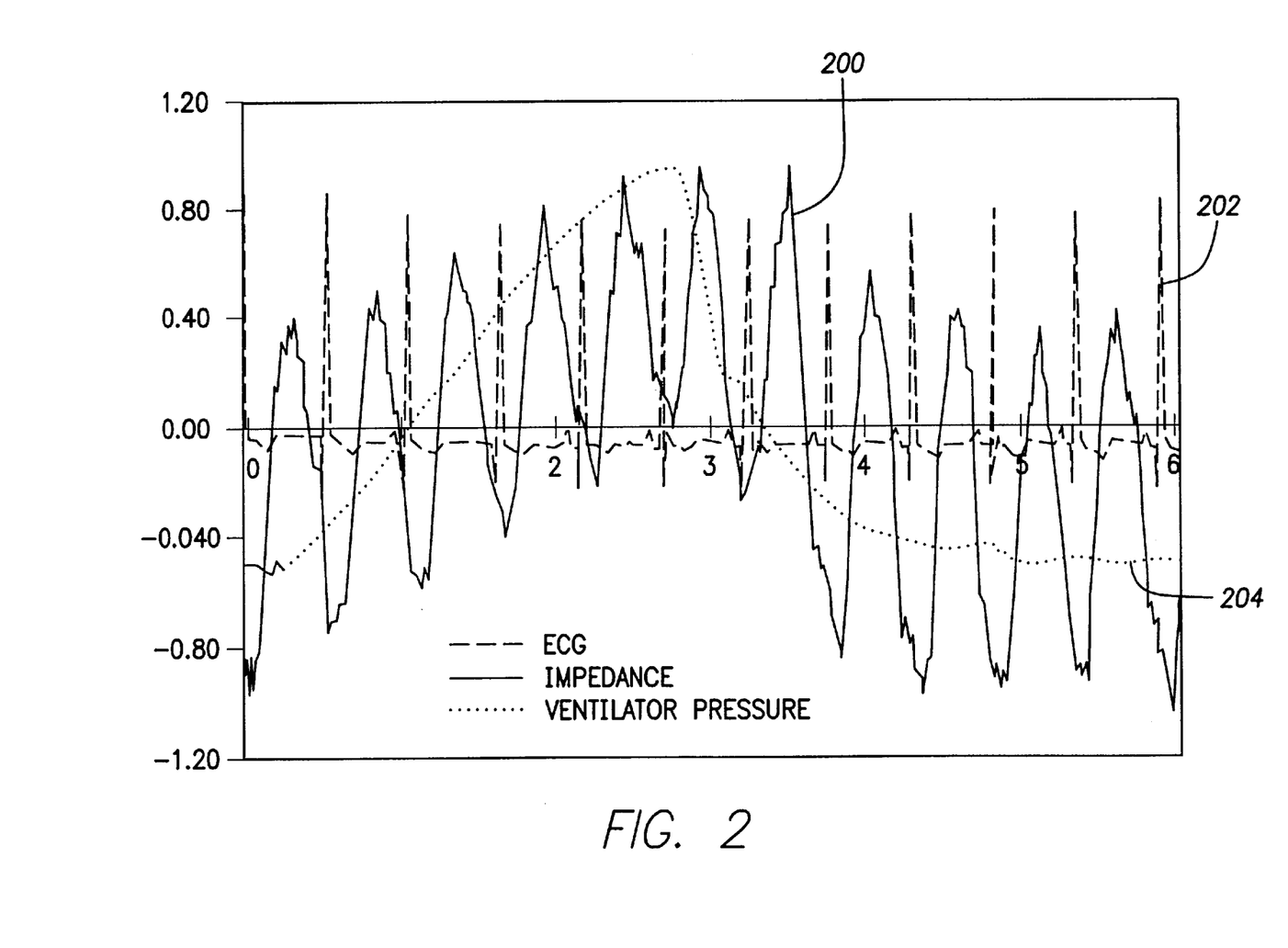
FIG. 2 is a graphical representation of a typical ECG, a typical transthoracic impedance measurement and a ventilation pressure signal superimposed on the same graph to illustrate the interrelation of the impedance signal to the ECG signal and the ventilation signal.

Unfortunately, measurement of the transthoracic impedance using the case electrode 108 and leads 104 in the manner described above will include a component corresponding to the motion of the heart. FIG. 2 illustrates a graphical representation of a measured transthoracic impedance signal 200 superimposed against an ECG signal 202 and a ventilator pressure signal 204 obtained during the same time period. The impedance signal 200 is preferably measured between the lead 104 and the casing 108 and it includes both components that are attributable to the beating of the heart and to the rise and fall of the chest during patient ventilation. In this particular measurement, the impedance signal 200 is comprised of a voltage that is measured between the casing 108 and the leads 104 and the variation of the voltage is the result of the changing impedance that is due to both the beating of the heart and the movement of the patient's chest during breathing. The ECG signal 202 is representative of the beating of the patient's heart and the ventilator pressure signal 204 is representative of the movement of the patient's chest as a result of the patient breathing and is obtained in a well-known manner.

As shown in FIG. 2, the impedance signal 200 varies significantly due to the beating of the patient's heart. In particular, the impedance signal 200 is essentially sinusoidal and, following each QRS complex of the ECG signal, the impedance signal 200 varies approximately 1.2 volts. Consequently, the transthoracic impedance signal includes a high frequency component that is due to the beating of the heart. However, FIG. 2 also illustrates that the peak positive/negative values of each high frequency cycle of the impedance signal 200 approximately tracks the ventilator pressure signal 204. In particular, the peak magnitude of each cardiac cycle of the impedance signal 200 rises in magnitude as the patient's chest expands while breathing and lowers in value when the patient's chest deflates so as to correspond with the ventilation pressure signal 204.

Hence, FIG. 2 demonstrates that the impedance signal 200 is comprised of essentially two components. One component is a higher frequency component that is due to the beating of the heart. The other component is the lower frequency component that is due to the movement of the chest of the patient during breathing. As is understood in the art, the frequency of the heart beating is generally at least four times greater than the frequency of the patient's breathing. Hence, in many prior art applications, minute ventilation parameters have been determined using low-pass filters so as to filter the higher frequency component of the transthoracic impedance that is due to the beating of the heart. However, the use of such filters is problematic as the filters consume limited power available from the battery of the implanted device and further occupy limited space within the casing 108 of the implanted device 100.

In one embodiment, the implanted cardiac device 100 is adapted to measure the transthoracic impedance using the impedance sensor circuit 123 at a sampling rate selected so that the impedance signal is periodically measured when the contribution of the heart signal 202 to the impedance signal 200 can be discounted or mathematically removed.

As will be discussed below in conjunction with FIGS. 3A and 3B, in one embodiment, the processor induces, or triggers, the impedance sensor 123 to measure the impedance when the contribution to the impedance due to the beating of the heart is negligible. As will also be discussed, in conjunction with FIG. 4 in another embodiment, the processor triggers the impedance sensor 123 to periodically measure the impedance at a frequency that is selected so that the contribution to the measured impedance resulting from the beating of the heart can be mathematically removed from the resulting impedance measurement. In both of these embodiments, an impedance signal can be constructed that is representative of the patient's respiration without requiring the use of additional filter elements.

In this way, a parameter can be obtained by the processor that is indicative of minute ventilation and the processor 110 can use this parameter to adjust the delivery of pacing pulses to the heart 16 so as to more closely match the heart rate to metabolic need.

Figure 3A:
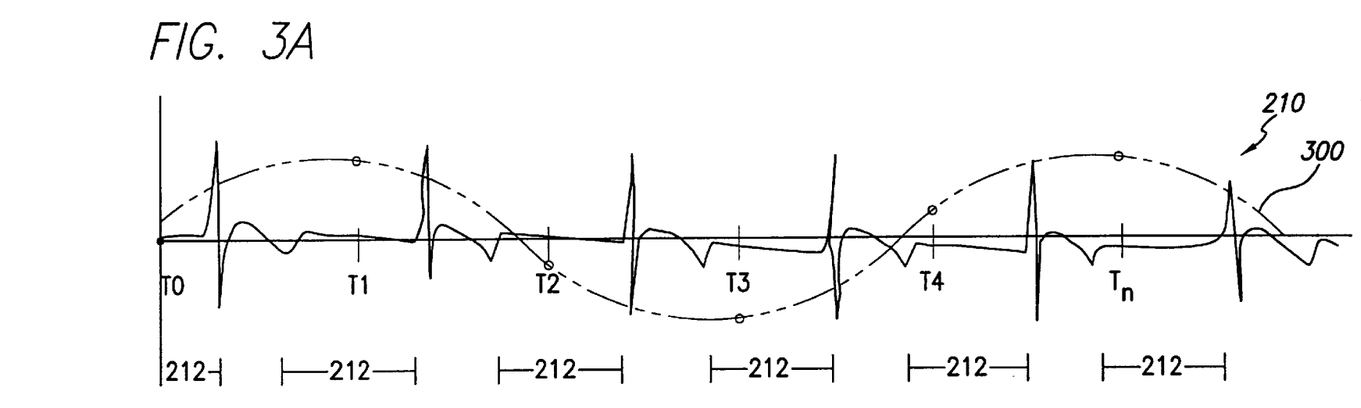
FIG. 3A is a graphical representation of the transthoracic impedance signal which comprises the respiratory signal superimposed on a time line with an IEGM signal provided by a sensor implanted within the heart of a patient.
Figure 3B:
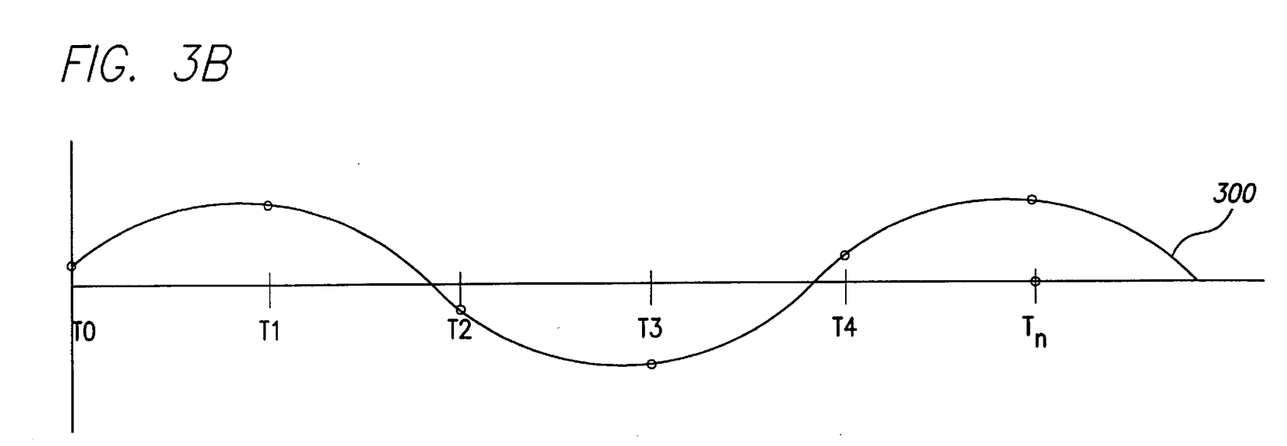
FIG. 3B is a graphical representation of a reconstructed transthoracic impedance signal.

In particular, FIGS. 3A and 3B illustrate an IEGM signal 210 that is provided to the processor 110 by the sensor 120. As discussed above, the sensor 120 provides an IEGM signal to the processor 110 to enable the processor 110 to determine whether to provide cardiac stimulation to the heart via the leads 104. The IEGM signal 210, in one embodiment, is measured using one of the implanted leads 104 in a manner that is known in the art.

As shown in FIG. 3A, the IEGM signal 210 has a plurality of quiescent periods 212 where the heart activity is at a minimum. It will be appreciated that during the quiescent periods 212, which is approximately late diastole period, the contribution of the heart to the impedance signal 200 (FIG. 2) can generally be discounted as negligible. Hence, in this embodiment, the processor 110 can induce the impedance circuit 123 (FIG. 1) to measure the transthoracic impedance between one of the implanted leads 104 and the casing 108 at times T1–Tn that are selected so that the resulting transthoracic impedance measurements are primarily due to movement of the chest as a result of respiration. These sampled values provide a respiration signal 300 to the processor 110 that can be used to optimize the pacing of the heart. In general, as the heart rate is typically on the order of at least four or more times faster than the respiration rate, at least four or more data points representative of the value of the transthoracic impedance resulting from respiratory motion, i.e., the minute ventilation parameter, can typically be obtained for each respiratory cycle.

Preferably, in this embodiment, the impedance measurements are taken during the heart's quiescent period. The processor 110 in one embodiment is synchronized so as to induce the impedance sensor circuit 123 (FIG. 1B) to periodically perform the impedance measurement at a fixed rate selected so that the measurements are taken during the quiescent period. Alternatively, the processor 110 can be adapted to induce the impedance sensor circuit 123 to obtain the impedance measurements after a pre-selected delay period following the occurrence of an R-wave or ventricular pacing pulse in the IEGM signal 210 from the sensor 120. In one embodiment, the pre-selected delay period would be on the order of 700 ms in order that the measurement occurred during a quiescent period where the heart's signal contribution to the overall transthoracic impedance measurement would be negligible.

Specifically, as shown in FIGS. 3A and 3B, to obtain the respiration signal 300, in this embodiment, samples are taken as described above using the case electrode 108 and the pacing leads 104 beginning at time T0. To ensure samples are taken during the quiescent periods 212 of the heart signal 210, the first sample should be synchronized with the beginning of the heart signal 210. In this embodiment, synchronization is obtained by beginning measurement of the respiration signal 300 upon detection of ventricular contraction of the heart. The processor 110 preferably uses the heart electrogram signal 210 provided by the sensor 120 implanted in the heart for synchronization purposes. This provides a set point from which sampling can be initiated.

In this embodiment, the processor 110 is adapted to sample the transthoracic impedance each time the heart component of the overall impedance measurement can be discounted as negligible. Hence, in this embodiment, the processor 110 triggers the minute ventilation sensor 123 (FIG. 1B) to obtain the impedance measurements at times T1–Tn during the quiescent periods 212 of the IEG signal 210. In the example shown in FIG. 3A, multiple measurements of the transthoracic impedance can be made for each ventilation cycle due to the higher heart frequency. Consequently, if the processor 110 is synchronized so as to sample at the predicted time periods where the heart's contribution to the impedance measurement is negligible, the resulting data points obtained will be indicative of the respiration impedance signal 300 and can therefore be used to provide a minute ventilation parameter to the processor 110.

The data points obtained can then be used to reconstruct the respiration signal 300 in the manner described in greater detail below. Basically, a curve-fitting algorithm is performed by the processor 110 using the data points sampled at times T0 to Tn. For example, in one embodiment, Nyquist's theorem is used to reconstruct the respiration impedance signal 300 using the sampled data points obtained during the quiescent periods of the heart signal 210. Nyquist's theorem allows a periodic signal to be reconstructed using a sampling rate that is at least twice the highest frequency component of the signal to be reconstructed. In the case of the respiration signal 300, there are possibly harmonics which would necessitate a sampling rate of approximately six times the expected frequency of the respiration signal 300 to allow a Nyquist's theorem based reconstruction of the respiration signal 300. Consequently, sampling at approximately twice the heart rate will allow for a reconstruction using Nyquist's theorem with a relatively high degree of accuracy.

The process by which the respiration signal 300 is reconstructed, in this embodiment, will now be described in reference to FIGS. 3A and 3B. In particular, once the processor 110 chooses the sampling rate and identifies a period where the heart's contribution to the transthoracic impedance signal is negligible, i.e., the quiescent periods 212 of the heart signal 210, sampling may begin. Samples are taken according to the sampling rate at time periods T0, T1, T2, T3, T4 until a preselected time period Tn. With a synchronized sampling rate, each of these samples should occur during the quiescent period 212 of the IEG signal 210. The respiration sampled signal 300 is created from a combination of the samplings at the points T0 through Tn.

As can be seen by FIG. 3A, each of the sample points taken along the IEGM signal 210 occur during the quiescent periods 212 of heart activity. As a result, the contribution of the heart activity to the measured impedance values is negligible. Consequently, the resulting signal is indicative of the respiration of the patient. Therefore, upon completion of the sampling, a complete respiratory waveform is available for the processor 110. Because the heart signal 210 is removed by the sampling rate, there is no need for an additional filter. By removing the filter from the pacemaker, space is saved in the pacemaker housing.

Further, the maximum sampling rate of twice the heart rates can result in only 2–4 samples per second, significantly lower than the previous 16–20 samples per second used to create the combination waveform 250 of FIG. 2. Each time the pacemaker takes a sample, a set amount of energy is expended. By decreasing the number of samples to obtain the waveform, the pacemaker conserves energy. This energy savings results in an overall extended useful life of the pacemaker.

Figure 4:
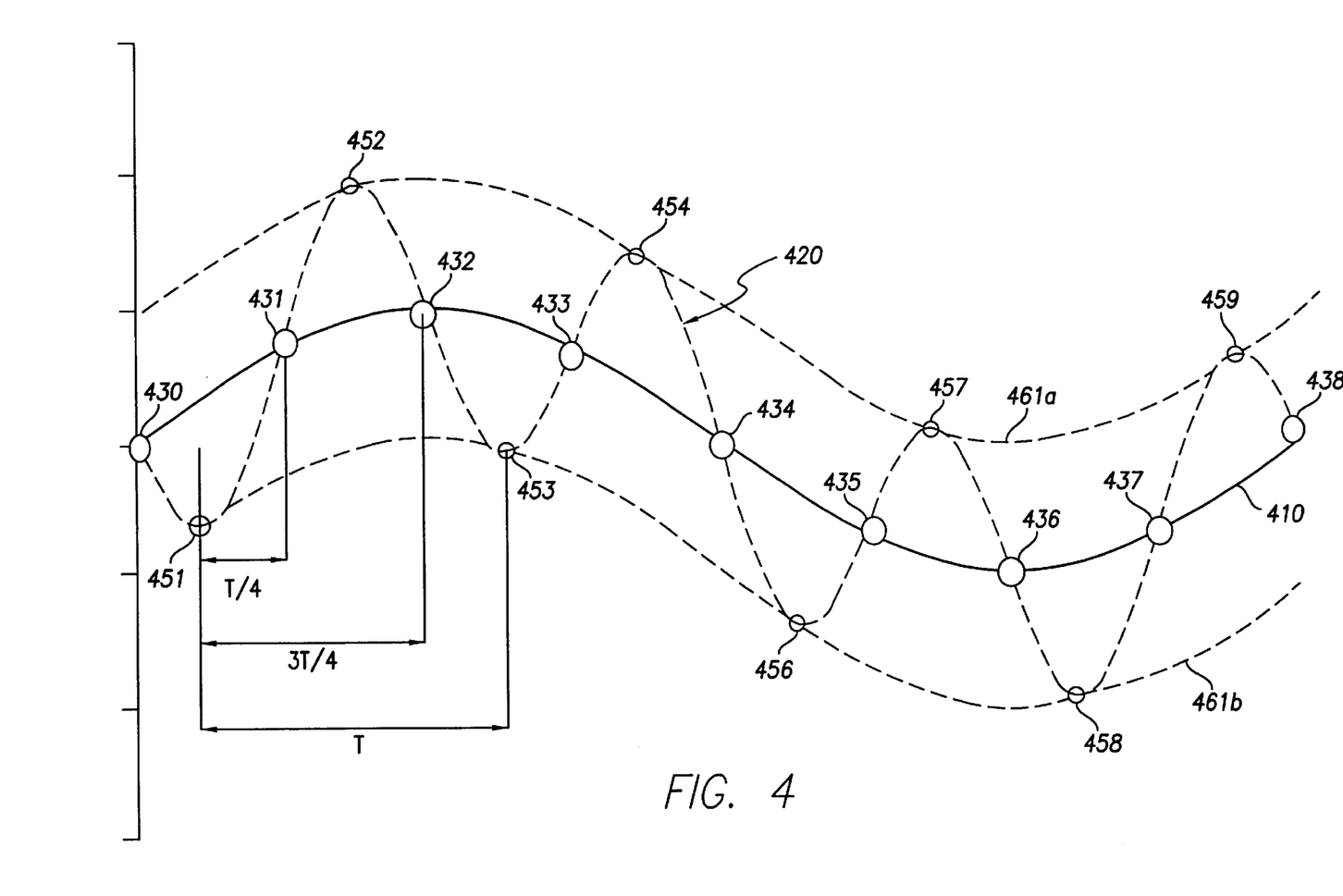
FIG. 4 is a graphical representation of a reconstructed transthoracic impedance signal superimposed on a timeline with the associated cardiac impedance signal also illustrated.

FIG. 4 illustrates an alternative manner of reconstructing a respiration signal 410. As is illustrated in FIG. 2, the impedance signal 200 is generally periodic. The higher frequency component of the impedance signal 200 resulting from the motion of the heart is also periodic. Hence, the combined impedance signal 200 can be modeled as the higher frequency heart component that is superimposed on the lower frequency respiration component. This phenomenon is better illustrated in FIG. 4 where the combined impedance signal 420 that would be measured by the impedance sensor 123 is superimposed over the respiration signal 410 that is of interest. As illustrated, the zero points 430–438 of the combined measured impedance signal 420 are generally positioned on the respiration impedance signal 410 such that, as the magnitude of the respiration impedance signal 410 increases and decreases, the magnitude at the zero points 430–438 of the higher frequency combined signal 420 also correspondingly increase and decrease.

The frequency of the component of the combined measured impedance signal 420 that is due to the motion of the heart is substantially the same as the frequency of the IEG signal received by the processor 110 from the sensor 120 (See, FIG. 1B). Periodically measuring the combined impedance 420 at the same interval during each period of the patient's heart beat will yield a plurality of data points that provide the shape of the underlying respiration signal 410 and can thus be used to reconstruct the respiration signal.

In particular, the period T of the high frequency combined impedance signal 420 corresponds to the period of the IEG signal produced by the sensor 120. In the example shown in FIG. 4, if the impedance is sampled at ¼ of the period T and ¾ of the period T, during each cycle of the IEG signal, the resulting impedance measurements will, in this example, result in the zero crossing points 431–438. These data points can be used to reconstruct the respiration component 410 of the combined impedance signal 420 and can thus be used to produce the minute ventilation parameters.

This process can be further illustrated with the data points 451 459. If the impedance sensor 123 periodically sampled the combined impedance signal 420 at the peaks of the combined impedance signal 420, the resulting data points fall within curves 461a, 461b that have the same general shape as the respiration impedance signal 410 and can thus be used to reconstruct a respiration signal without requiring the use of high frequency filters.

It will be appreciated that the sampling can occur at essentially any interval during the period T, provided that for subsequent cycles of the IEG signal, the sampling occurs at the same interval during each subsequent cycle. By selecting the same interval for sampling during each heart cycle, the contribution to the combined measured impedance signal 420 due to the heart component is a constant that can be discounted to develop a respiration signal that can be used to calculate a minute ventilation parameter. It will be appreciated, however, that a preferred interval will occur when the signal 420 is changing the least such that variations from cycle to cycle is reduced. A curve can then be fit to the resulting data points to produce the impedance signal that corresponds to the patient's respiration.

Figure 5:
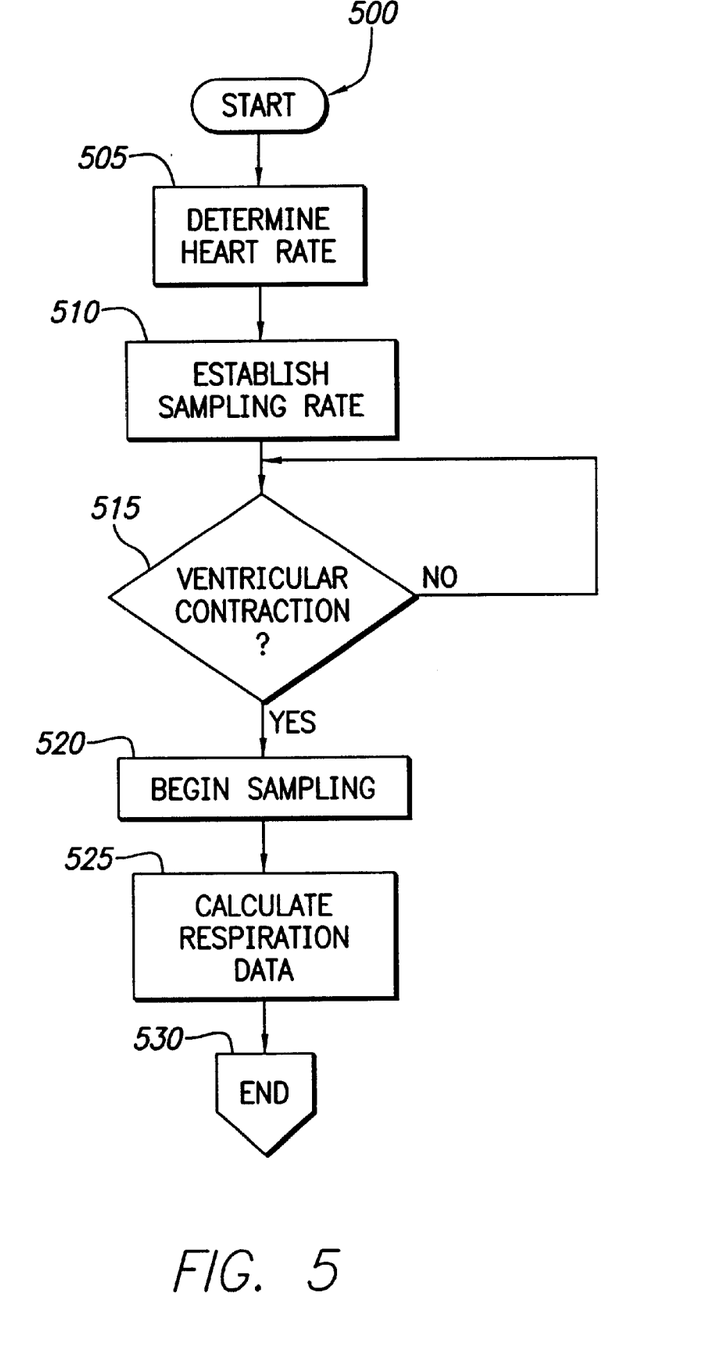
FIG. 5 is a flow diagram illustrating the procedures to obtain minute ventilation data of the present invention.

The flow chart of FIG. 5 illustrates one exemplary operation of the processor 110 as it obtains a transthoracic impedance measurement in either of the above-described manners. After initialization at the start state 500, the processor 110 determines the current heart rate as indicated by activity state 505. The processor 110 contains hardware and/or software allowing determination of the heart rate. After the heart rate is determined, the processor 110 establishes a sampling rate as indicated by activity state 510 that is adapted to sample the impedance between one of the leads 104 and the casing 108. As discussed above, the sampling rate can either be selected so that the sampling occurs during the quiescent period of heart activity, i.e., a period when the heart's contribution to the measured impedance is minimized, or it can be an interval selected such that repeated samplings can result in the reconstruction of the respiration signal in the manner described in conjunction with FIG. 4.

As discussed above, the sampling rate preferably ranges from twice the frequency of the respiration signal to twice the frequency of the heart signal. In practical terms, this sampling rate generally ranges from approximately one beat per second to five beats per second. In one embodiment, the sampling rate is chosen according to Nyquist's theorem to ensure that significant samples are taken to permit reconstruction of the respiration impedance signal. Generally, the sampling rate is twice the heart rate.

Once the heart rate and sampling rate are determined in the present invention, the sampling rate must be synchronized with the heartbeat. To obtain synchronization, the pacemaker senses if a ventricular contraction has occurred as indicated by a decision state 515. The pacemaker looks for either the presence of an R-wave, or, in absence of an R-wave, the presence of a pacing spike causing ventricular capture to determine if a ventricular contraction occurred. If no-ventricular contraction is seen, the pacemaker will continue sensing until ventricular contraction occurs.

After detection of ventricular contraction, the present invention begins sampling as indicated by activity state 420. Beginning the sampling immediately following ventricular contraction synchronizes the sampling rate with the heart signal. As discussed above, the processor 110 can be adapted to sample at a rate that is selected so that the samples are obtained at T0–Tn (FIGS. 3A, 3B) where the IEGM signal 210 of the heart indicates a quiescent period 212. Alternatively, the processor 110 can be adapted to induce the sampling of the impedance at regular intervals in the manner disclosed in FIG. 4. If the heart rate is relatively constant, a constant sampling rate selected in state 510 will yield periodic samples at regular intervals. However, it will be appreciated that if the heart rate is varying, the sampling rate 510 may have to be changed so as to ensure that the sample is taken during the time period at an interval selected to ensure the sampling occurs at the same basic interval of each period of the heart signal. Alternatively, the sampling may be performed by having the processor 110 trigger the impedance measurement circuit 123 to obtain the impedance measurement at a delay period from the occurrence of an R-wave where the delay period is selected so as to result in the impedance being sampled at a time where the heart's contribution to the impedance can be discounted.

As discussed above, the sampled signal will correspond to the respiration signal. After the samples are taken, the processor 110 can mathematically reconstruct the respiration signal using the sample data points and can then calculate the minute ventilation parameter or data from the sampled signal as indicated in activity state 525. In one embodiment, the minute ventilation data is the amplitude times the frequency of the respiration signal which provides an indication of the volume of air that is being inhaled by the patient. After calculating the minute ventilation data, the processor 110 moves to the end state 530. At this point, the processor 110 can adjust the heart rate accordingly due to the minute ventilation data indicating a change in patient activity in a well-known manner.

Numerous variations and modifications of the invention will become readily apparent to those skilled in the art. Accordingly, the invention may be embodied in other specific forms without departing from its spirit or essential characteristics. The detailed embodiment is to be considered in all respects only as illustrative and not restrictive and the scope of the invention is, therefore, indicated by the appended claims rather than by the foregoing description. All changes, which come within the meaning and range of equivalency of the claims, are to be embraced within their scope.

What is claimed is:

1. An implantable cardiac device for delivering electrical stimulation to the heart, the device comprising:

a sensing circuit adapted to detect a heart signal indicative of electrical activity of the heart;

an impedance sensor adapted to measure a body parameter that is indicative of the ventilation and cardiac activity of the patient and provide an unfiltered impedance signal indicative thereof; and a processor which receives the unfiltered impedance signal and the heart signal, wherein the processor is adapted to use the heart signal and the impedance signal to control the delivery of therapeutic stimulation to the heart, wherein the processor is further adapted to trigger the minute ventilation sensor to measure the body parameter indicative of the ventilation and cardiac activity during intervals of time selected so that the contribution to the impedance signal resulting from the action of the heart can be discounted so as to allow the processor to develop a minute ventilation parameter from the unfiltered impedance signal.

2. The device of claim 1, wherein the processor receives a plurality of samples comprising the unfiltered impedance signal and uses the plurality of samples to develop the minute ventilation parameter.

3. The device of claim 1, wherein the measurement of the body parameter by the impedance sensor occurs at a rate that is approximately twice the rate of the heart signal.

4. The device of claim 1, wherein the body parameter indicative of minute ventilation comprises transthoracic impedance.

5. The device of claim 4, further comprising a case electrode and wherein the transthoracic impedance is periodically sampled by delivering a pulse from the at least one lead to the case electrode.

6. The device of claim 4, wherein the sensing circuit provides a IEGM signal to the processor and the processor triggers the impedance sensor to measure the transthoracic impedance during a period of time where the contribution to the transthoracic impedance measurement due to the heart activity is negligible.

7. The device of claim 6, wherein the processor is adapted to induce the impedance sensor to measure the transthoracic impedance during the quiescent periods of the heart as indicated by the heart signal.

8. The device of claim 6, wherein the sensing circuit detects a heart signal that is periodic and wherein the processor triggers the impedance sensor to sample the transthoracic impedance at a selected interval during each cycle of the heart signal.

9. The device of claim 8, wherein the processor uses the transthoracic impedance signals sampled at the selected interval during each cycle of the heart signal to develop a respiration impedance signal indicative of the component of the transthoracic impedance that is due to the ventilation activity of the patient.

10. The device of claim 9, wherein the processor triggers the minute ventilation signal to sample the transthoracic impedance at ¼ and ¾ of the period T of each cycle of the heart signal.

11. An implantable cardiac device for delivering electrical stimulation to the heart of a patient, the device comprising:

means for stimulating the heart of a patient;

sensing means for providing a signal indicative of the function of the heart;

ventilation means for measuring a body parameter indicative of the patient's ventilation and for providing a parameter signal indicative thereof;

processing means for processing the parameter signal from the ventilation means to develop a ventilation parameter, wherein the processing means induces the ventilation means to measure the body parameter during time periods when the contribution of the heart to the body parameter can be discounted so that the ventilation parameter can be developed by the processing means without filtering to remove the contribution of the heart to the ventilation parameter.

12. The device of claim 11, wherein the sensing means provides an intracardiac electrogram signal to the processing means and the processing means uses the intracardiac electrogram signal to induce the ventilation means to measure the body parameter during a quiescent period of the heart's activity.

13. The device of claim 12, wherein the means for stimulating the heart of the patient comprises at least one lead adapted to be positioned in the heart of the patient and further adapted to provide pacing pulses to the heart of the patient.

14. The device of claim 13, wherein the processing means is positioned within a casing that is adapted to be implanted in the body of the patient.

15. The device of claim 14, wherein the ventilation means measures the transthoracic impedance between the at least one lead and the casing.

16. The device of claim 11, wherein the processing means receives a plurality of parameter signals from the ventilation means so that the processing means develops the ventilation parameter from the plurality of parameter signals.

17. The device of claim 16, wherein the ventilation means is adapted to obtain at least four parameter samples during each respiration cycle and wherein the processing means is adapted to use the at least four parameter samples to develop the ventilation parameter.

18. The device of claim 11, wherein the processing means uses the signal from the sensing means to determine the frequency of a heart impedance signal which corresponds to the heart contribution to the ventilation parameter and wherein the processing means uses the signal from the sensing means to induce the ventilation means to measure the body parameter at approximately the zero crossings of the heart impedance signal.

19. The device of claim 11, wherein the ventilation means measures the transthoracic impedance of the patient and provides the parameter signal that is indicative of the transthoracic impedance, wherein the parameter signal includes a component of the transthoracic impedance that is due to the patient's heart activity and a component of the transthoracic impedance that is due to the patient's ventilation activity.

20. The device of claim 19, wherein the processing means uses the signal from the sensing means to determine the frequency of a heart impedance signal which corresponds to the component of the transthoracic impedance that is due the patient's heart activity and wherein the processing means uses the sensor signal to induce the ventilation means to measure the transthoracic impedance at a selected interval during each cycle of the heart impedance signal such that a ventilation impedance parameter can be developed by the processing means.

21. The device of claim 20, wherein the processing means develops a ventilation impedance signal by fitting a curve to the measured transthoracic impedance wherein the curve corresponds to the component of the transthoracic impedance that is due to the patient's ventilation activity.

22. The device of claim 20, wherein the processing means uses the ventilation impedance signal curve to determine a minute ventilation parameter.

23. An implantable cardiac device, comprising:

a sensor adapted to obtain a heart signal indicative of the action of the heart;

an impedance measurement circuit that obtains transthoracic impedance measurements; and a control unit that receives the heart signal and triggers the impedance measurement circuit to obtain the impedance measurements during a time period selected based on the heart signal so that the contribution to the impedance measurement due to the activity of the heart is negligible so that the impedance measurement is primarily indicative of the respiration of the patient, the control unit further programmed to control stimulation therapy based on the impedance measurement.

24. The device of claim 23, wherein the control unit is positioned within a casing that is adapted to be implanted within the body of a patient and wherein the impedance measurement circuit measures the impedance between at least one implantable lead electrode and the casing.

25. The device of claim 24, wherein the sensor obtains an IEGM signal from the at least one lead electrode.

26. The device of claim 25, wherein the control unit evaluates the IEGM signal and triggers the impedance measurement circuit to measure the transthoracic impedance during a time period when the IEGM signal indicates a quiescent period for the heart.

27. The device of claim 26, wherein the control unit triggers the impedance measurement circuit to obtain the transthoracic impedance measurement after a pre-selected delay period following the heart signal indicating the occurrence of an R-wave.

28. The device of claim 27, wherein the delay period is approximately 700 ms.

29. The device of claim 23, wherein the control unit is adapted to obtain at least four data points for each respiration cycle of the patient and then use these four data points to mathematically reconstruct a respiration waveform of the patient.

30. The device of claim 29, wherein the control unit is adapted to obtain a minute ventilation parameter from the reconstructed respiration waveform of the patient.

31. A method of obtaining a ventilation parameter for an implantable cardiac device which can be used to provide therapeutic stimulation to the heart of the patient, the method comprising:

obtaining a heart signal indicative of the electrical function of the heart;

evaluating the heart signal so as to determine a quiescent time period;

periodically measuring the transthoracic impedance of the patient during the quiescent time period, wherein the quiescent time period is selected so that the contribution of the heart to resulting impedance measurement is reduced such that an impedance measurement indicative of the patient's ventilation can be obtained with reduced filtering of the sampled measurement; and processing the periodically obtained impedance measurements to produce a ventilation parameter that can be used to vary the delivery of therapeutic stimulation to the heart of the patient.

32. The method of claim 31, wherein obtaining a heart signal comprises obtaining an IEGM signal from a lead implanted in the heart.

33. The method of claim 32, wherein evaluating the heart signal so as to determine a quiescent period comprises:

determining the occurrence of an R-wave; and measuring a delay period following the occurrence of the R-wave, wherein the delay period is selected so that the quiescent time period corresponds to the delay period following the occurrence of the R-wave.

34. The method of claim 31, wherein periodically measuring the transthoracic impedance of the patient comprises sending a impedance measurement waveform from the lead implanted to a case electrode within the body of the patient.

35. The method of claim 34, wherein periodically measuring the transthoracic impedance measurement comprises obtaining at least four impedance measurements during each ventilation cycle of the patient.

36. The method of claim 35, wherein processing the periodically obtained impedance measurements to obtain the ventilation parameter comprises mathematically reconstructing a ventilation signal corresponding to the ventilation of the patient.

37. The method of claim 36, wherein processing the periodically obtained impedance measurement further comprises producing a minute ventilation parameter from the ventilation signal.

38. The method of claim 37, further comprising adjusting the delivery of therapeutic stimulation to the heart based at least in part on the minute ventilation parameter.

39. A method of obtaining a ventilation parameter for an implantable cardiac device which can be used to provide therapeutic stimulation to the heart of the patient, the method comprising:

obtaining a heart signal indicative of the function of the heart;

evaluating the heart signal so as to determine the frequency of the heart signal and the corresponding period;

periodically measuring the transthoracic impedance of the patient at a selected interval during each period of the heart signal such that the resulting transthoracic impedance measurements are indicative of the patient's ventilation activity; and processing the periodically obtained transthoracic impedance measurements so as to obtain a curve that corresponds to the component of the transthoracic impedance that is the result of the patient's ventilation activity without filtering the heart component of the transthoracic impedance measurements.

40. The method of claim 39, wherein obtaining a heart signal comprises obtaining an IEGM signal from a lead implanted in the heart.

41. The method of claim 39, wherein periodically measuring the transthoracic impedance comprises obtaining at least four impedance measurements during each ventilation cycle of the patient.

42. The method of claim 39, further comprising evaluating the curve that corresponds to the component of the transthoracic impedance that is the result of the patient's ventilation activity so as to produce a minute ventilation parameter from the curve.

* * * * *